United States Patent [19]

Jennings

[11] Patent Number: 4,577,622

[45] Date of Patent: Mar. 25, 1986

[54] ANTI-SHOCK TREATMENT METHOD AND GARMENT

[76] Inventor: Thomas J. Jennings, 5011c Cheswick, Dayton, Ohio 45431

[21] Appl. No.: 630,159

[22] Filed: Jul. 12, 1984

[51] Int. Cl.$^4$ .................. A61F 13/08; A61H 11/00
[52] U.S. Cl. .................. 128/24 R; 128/134; 128/DIG. 15; 128/67
[58] Field of Search ............ 128/24 R, DIG. 15, 134, 128/67

[56] References Cited

U.S. PATENT DOCUMENTS

| | | | |
|---|---|---|---|
| 2,379,497 | 7/1945 | Sellmeyer | 128/24 R |
| 2,495,316 | 1/1950 | Clark et al. | 128/1 |
| 2,528,843 | 11/1950 | Poor | 128/24 R |
| 2,533,504 | 12/1950 | Poor | 128/24 R |
| 3,218,103 | 11/1965 | Boyce | 128/134 |
| 3,358,141 | 12/1967 | Hoffmann | 128/DIG. 15 |
| 3,391,692 | 7/1968 | Spielberg | 128/24 R |
| 3,548,809 | 12/1970 | Conti | 128/24 R |
| 3,659,593 | 5/1972 | Vail | 128/64 |
| 3,826,249 | 7/1974 | Lee | 128/24 R |
| 3,856,008 | 12/1974 | Fowler et al. | 128/165 |
| 3,867,930 | 2/1975 | Brown | 128/83 |
| 3,892,399 | 7/1975 | Cabansag | 128/134 |
| 3,933,150 | 1/1976 | Kaplan et al. | 128/24 R |
| 4,355,632 | 10/1982 | Sandman | 128/24 R |
| 4,407,276 | 10/1983 | Bledsoe | 128/DIG. 15 |

Primary Examiner—Clyde I. Coughenour
Attorney, Agent, or Firm—Donald J. Singer; Thomas L. Kundert; John R. Flanagan

[57] ABSTRACT

An improved anti-shock treatment method and garment employ a series of resilient, stretchable straps and belts attached to semi-rigid elongated support rods positionable along the midline of the outer sides of the legs and abdomen of a shock victim. The support rods are each formed of two elongated parts which are connected together but can be slid relative to one another to adjust the lengths of the support rods to the combined length of the victim's leg and abdomen. By applying the straps to the legs and the belts to the abdomen of the victim, starting at the feet of the victim and proceeding upwardly to just below the victim's ribs, a milking action is created on the blood in the lower body of the victim which enhances blood return from the lower body to the victim's heart.

3 Claims, 5 Drawing Figures

ANTI-SHOCK TREATMENT METHOD AND GARMENT

RIGHTS OF THE GOVERNMENT

The invention described herein may be manufactured and used by or for the Government of the United States for all governmental purposes without the payment of any royalty.

BACKGROUND OF THE INVENTION

1. Field of the Invention

The present invention broadly relates to the emergency treatment of victims suffering from shock and, more particularly, is concerned with an anti-shock treatment method and garment for sequentially applying pressure to the legs and abdomen of the victim to cause a "milking action" thereon which forces blood return to the heart.

2. Description of the Prior Art

The use of a garment for applying pressure to the extremities of a person and thereby control blood flow is known as shown by U.S. patents to Clark et al (U.S. Pat. No. 2,495,316), Vail (U.S. Pat. No. 3,659,593), Fowler et al (U.S. Pat. No. 3,856,008), Kaplan et al (U.S. Pat. No. 3,933,150) and Sandman (U.S. Pat. No. 4,355,632). The garments of Kaplan et al and Sandman are specifically directed to the treatment of shock.

Shock is a clinical state where the tissues of the body are not adequately perfused by blood and become hypoxic (low oxygen state). The treatment of shock is to increase the blood volume so that tissue perfusion is restored. The garments of Kaplan et al and Sandman, as well as such garment as the Military Anti-Shock Trouser (MAST), help in the treatment of shock in a number of ways. The anti-shock garments apply pressure to the victim's legs and abdomen in order to increase the blood return to the heart and to decrease perfusion of the lower body portion. The garments, to some degree, inherently stabilize leg and/or pelvic fractures. Splinting of fractures is not only beneficial from an orthopedic standpoint, but also prevents further blood loss from the fracture site. Finally, anti-shock garments apply pressure to internal and external bleeding sites in the lower portion of the body which helps stop bleeding.

However, present commercially-available anti-shock garments of the kind represented by the garments of these two patents and the MAST have two problems associated with their use. The most important problem which has been demonstrated in the case of the MAST garment is that it does not accomplish its major goal of mobilizing blood from the lower portion of the body effectively. Experiments have shown that only about one-quarter of the blood which exists in the legs alone is returned to the heart by use of the MAST garment. Two factors contribute to this poor result. First, pressure applied to the leg is probably not evenly distributed. This condition might be due to differences in the diameters of various portions of the leg. Also, the pressure on the thigh is generated sooner, and will usually be higher, than the pressure on the calf. Secondly, the pressure is not applied in a distal to proximal direction so that the blood is not "milked" from the legs and abdomen.

Another problem with most commercially-available anti-shock trouser garments is that they must be inflated in order to pressurize the system. Punctures in the garment bladders, hoses and foot pump as well as leaky valves result in the loss of air pressure. As a result, the garment loses clinical efficacy. Since broken glass and sharp rocks are often found at an accident site, this is an important consideration. Also, changes in temperature and altitude will alter the garment's pressure.

Consequently, a need exits for an improved anti-shock treatment technique and garment which enhances blood return to the victim's heart and avoids the above-mentioned problems associated with presently available garments.

SUMMARY OF THE INVENTION

The present invention provides an anti-shock method and garment designed to satisfy the aforementioned needs. The unique feature of the present invention is the sequential application of pressure to the legs and abdomen of a victim from a distal to proximal direction thus enhancing blood return to the victim's heart. Particularly, a series of flexibly resilient, stretchable straps and belts are utilized which cause the pressure to be evenly applied to the body regardless of the diameter of that portion of the body. At the same time, the garment employing the resilient straps provides equal if not superior stabilization of leg and pelvic fractures. Also, if the necessity arises the garment can be used as a tourniquet. With present garments, they must be removed for effective tourniquet application. Finally, the improved garment of the invention allows the placement of a dressing on an external wound after the garment has been placed on the victim. Further, the external dressing can be added to or changed after the garment is on the person.

Accordingly, the present invention is directed to an improved anti-shock treatment method and garment which employs a series of flexible, resiliently-stretchable and adjustable straps and belts attached to semi-rigid elongated support members positionable along the outer lateral midline of the legs and abdomen of the victim. The support members are each formed of two elongated parts having mating means which allow sliding engagement of one part with the other. Specifically, one part has a rail defined along a side thereof and the other part has a groove defined along a side thereof which faces the side on the one part with the rail. With the rail fitted in the groove, the parts can slide relative to, and along, one another so as to adjust the lengths of the support members to the combined length of the victim's leg and abdomen.

More particularly, a plurality of straps are attached to and extend in opposite directions from opposite lateral edges of the one part which will be the lower part of the support member disposed along each leg of the person. The free ends of the straps contain fastening material so that respective ends of corresponding straps once encircled about a victim's leg from opposite directions can be attached to one another in overlapped fashion. By applying the straps to the leg from the lowest to the highest, pressure is applied so as to create a milking action on the leg which directs blood flow in an upward direction along and from the leg. The amount that the straps are stretched in applying them to the leg determines the tension which is applied uniformly around that portion of the leg.

A plurality of belts are attached to at least one of the parts of the support members which will become the upper parts thereof which extend along the sides of the waist and abdomen of the victim. Both ends of the belts contain fastening material so that the ends of each belt can be overlapped and attached after encircled about the abdomen of the person. The belts are applied starting with the lowermost one after the straps have been applied to the legs. This sequence will continue the milking action previously initiated at the ankles of the victim.

DETAILED DESCRIPTION OF THE INVENTION

Figure 1:
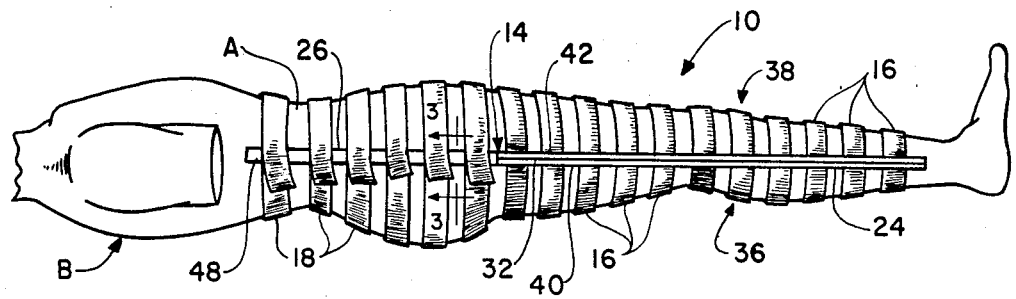
FIG. 1 is a side elevational view showing the improved anti-shock treatment garment of the present invention applied to legs and abdomen of a victim's body.
Figure 2:
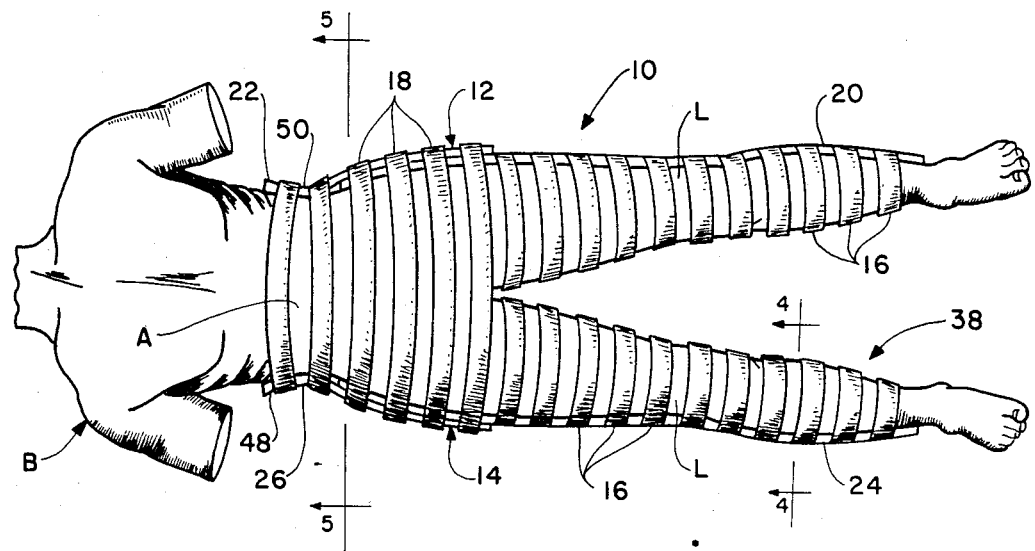
FIG. 2 is a top plan view of the improved anti-shock treatment garment applied to the legs and abdomen of the victim's body.

Referring now to the drawings, and more particularly to FIGS. 1 and 2, there is shown the preferred embodiment of the improved anti-shock garment of the present invention, being generally designated 10. The garment 10 includes a pair of support members in the form of elongated rods 12,14 and a plurality of adjustable straps 16 and belts 18 associated with the rods. Each rod 12,14 has two elongated parts 20,22 and 24,26. During use, the rods are each positioned along the lateral midline of opposite sides of the legs and abdomen of the victim's body B. Parts 20,24 which are disposed adjacent the legs will be referred to as lower parts, while parts 22,26 which are disposed adjacent the sides of the abdomen will be referred to as upper parts.

Figure 3:
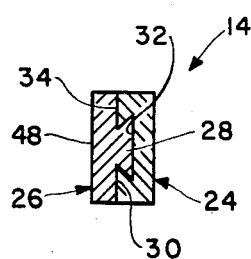
FIG. 3 is an enlarged sectional view of the interengaged upper and lower parts of each of the side support members of the improved garment as taken along line 3—3 of FIG. 1.

The parts of each rod 12,14 having mating means which allow sliding engagement of one part, such as each upper part 22,26, with the other part, such as each lower part 20,24. Specifically, in its preferred form as seen in FIG. 3, the mating means associated with each rod 12,14 comprises a rail 28 defined along a side 30 of the upper part 22,26 and a groove 32 defined along a side 34 of the lower part 20,24 which faces the upper part side 30 when the respective parts are interengaged with one another. The cross sections of the rail 28 and groove 32 have complementary configurations which only allow sliding movement of the parts of each rod 12,14 in the direction in which the rod extends. Thus, movement of the parts of a given rod relative to one another will either result in lengthening or shortening of the overall rod. In such manner, the lengths of the rods can be adjusted to the combined length of the victim's legs and abdomen.

Figure 4:
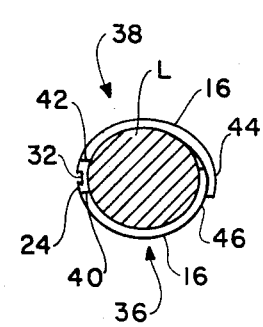
FIG. 4 is an enlarged sectional view of a pair of straps of the garment attached about the calf of the victim's leg as taken along line 4—4 of FIG. 2.

Each lower part 20,24 of each rod 12,14 has a first and second pluralities 36,38 of straps 16 attached to and extending perpendicularly in opposite directions from opposite lateral edges 40,42 of the lower part. The free ends 44,46 of straps 16 contain fastening material, such as pile and hook material sold under the trademark VELCRO, such that once the straps have encircled a portion of the victim's leg L from opposite directions, such as seen in FIG. 4, the ends 44,46 can be attached to each other in overlapped fashion. Furthermore, by applying the straps 16 about the legs L of the victim, starting at the lowermost straps adjacent the ankles, proceeding upwardly one set of straps at a time, and ending with the set of straps adjacent the crotch of the victim, a milking action or effect is created on the blood contained in the leg which directs blood flow in an upward direction along and from the leg. The straps 16 are made from flexible, resilient and stretchable material, such as rubber for instance. Therefore, the tension uniformly imposed about the portion of the leg when a particular set of straps is applied thereto depends on the amount that the straps are stretched before they are fastened together.

Figure 5:
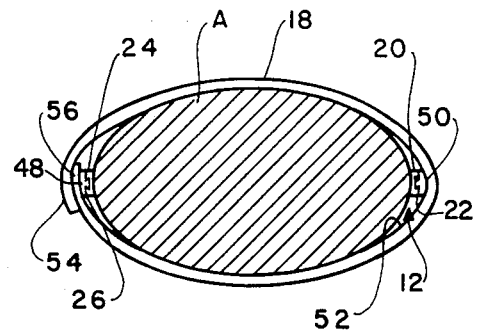
FIG. 5 is an enlarged sectional view of a belt of the garment attached about the abdomen of the victim as taken along line 5—5 of FIG. 2.

Each upper part 22,26 of each rod 12,14 has a belt 18 associated with it. Preferably, as seen in FIG. 5, the belt 18 is attached to the outwardly facing side of the upper part of one rod, for instance the outer side 48 of the upper part 22 of rod 12, and is fastened to the outwardly facing side of the upper part of the other rod, for example the outer side 50 of the upper part 26 of rod 14, when the belt 18 is encircled about the abdomen A of the victim's body B. The outer side 50 of the upper part 26 and the inner surface 52 of the belt 18 both contain suitable fastening material, such as the aforementioned hook and pile material, for accomplishing the fastened condition. Also, both ends 54,56 of the belt 18 contain the same fastening material so that the ends can be attached together in overlapped relationship after the belt 18 is applied about the abdomen of the person. The belts 18 are preferably formed from the same material as the straps, so the amount of tension applied depends on the amount each belt is stretched before the ends are fastened together. As in the case of the straps, the belts 18 are applied starting with the lowermost one just above the crotch after all straps have been applied to the legs and ending with the highest one just below the ribs of the victim.

This distal to proximal sequence will continue the milking action previously initiated at the ankles of the victim. The milking action on the lower body of the victim promotes optimal return of blood to the victim's heart. It is readily apparent that the garment could easily be converted into a tourniquet by pulling more tightly on any of the leg straps 16. Also, by use of resiliently stretchable material, such as rubber, pressure is applied substantially evenly to the portions of the legs and abdomen. The rods are preferably molded using a suitable plastic material which is semi-rigid or bendable, but tends to return to its linear shape. Thus, the rods would provide a suitable splint for leg and/or pelvic fractures. Also, in the case of the improved garment, dressings could be augmented, changed, etc., simply by loosening and then refastening the appropriate straps and/or belts. Further, it should be understood that the improved anti-shock treatment garment is intended to be applied directly over the clothing of the victim.

It is thought that the improved anti-shock method and garment of the present invention and many of its attendant advantages will be understood from the foregoing description and it will be apparent that various changes may be made in the form, construction and arrangement of the steps and parts thereof without departing from the spirit and scope of the invention or sacrificing all of its material advantages, the form hereinbefore described being merely a preferred or exemplary embodiment thereof.

Having thus described the invention, what is claimed is:

1. An improved anti-shock treatment method, consisting of the steps of:
    (a) supporting a series of resilient, stretchable straps on a first set of rods positioned along the midline of the outer side of each of the legs of a shock victim;
    (b) stretching each of said straps about a portion of each leg;
    (c) detachably fastening each strap about said leg portion in a stretched condition which applies pressure about said leg portion;
    (d) applying each strap in a stretched condition about an adjacent portion of each leg in a sequence beginning with a lowermost strap and proceeding strap by strap upwardly along said leg so as to create a milking action on blood contained within said leg which tends to return the same to the heart of said victim;
    (e) supporting a series of resilient, stretchable belts on a second set of rods slidably interconnected with said first set of rods and positioned along the midline of the outer sides of the abdomen of said victim;
    (f) stretching each of said belts about a portion of the abdomen;
    (g) detachably fastening each belt about said abdomen portion in a stretched condition which applies pressure about said abdomen portion; and
    (h) applying each belt in a stretched condition about an adjacent portion of the abdomen in a sequence beginning with a lowermost belt and proceeding belt by belt upwardly along said abdomen after application of the sequence of straps has been completed so to continue creation of the milking action on blood contained in the abdomen of the victim.

2. An improved adjustable anti-shock treatment garment for creating a milking action on the blood in the lower body of a shock victim solely by application of mechanical pressure to the lower body, said garment comprising:
    first and second pairs of elongated support members positionable along the midline of outer sides of the legs and abdomen, respectively of the shock victim;
    a plurality of resilient, stretchable straps attached to said first pair of support members and extending in opposite direction therefrom, said straps including ends fastenable together with said straps in stretched conditions encircling said legs so as to apply pressure about said leg in a sequence beginning with the lowermost strap and proceeding strap by strap upwardly along said legs;
    a plurality of resilient, stretchable belts attached to said second pair of support members and extendable about the abdomen of said shock victim, said belts including ends fastenable together with said belts in stretched conditions encircling said abdomen so as to apply pressure about said abdomen in a sequence beginning with the lowermost belt and proceeding belt by belt upwardly along said abdomen;
    said first and second pairs of support members including interengaging means which connect together but allow said members to slidably move relative to one another.

3. The garment as recited in claim 2, wherein said interengaging means is in the form of a rail disposed along one of said pairs of support members and a groove defined along the other pair of support members, the cross sections of said rail and groove having complementary configurations which only allow movement in the direction of the longitudinal extent of said each support member.

* * * * *